United States Patent [19]
Brunfeld et al.

[11] Patent Number: 5,459,576
[45] Date of Patent: Oct. 17, 1995

[54] DIFFERENTIAL PHASE CONTRAST INSPECTION SYSTEM

[75] Inventors: Andrei Brunfeld, Farmington Hills, Mich.; Gregory Toker, Jerusalem, Israel; Zvi Yaniv, Farmington Hills, Mich.; Ilan Laver, Kfar Saba, Israel

[73] Assignee: Display Inspection Systems, Inc., Wixom, Mich.

[21] Appl. No.: 185,123

[22] Filed: Jan. 24, 1994

[51] Int. Cl.⁶ .................................................. G01B 9/02
[52] U.S. Cl. ........................... 356/353; 356/359; 359/370
[58] Field of Search ................................... 356/345, 353, 356/359, 237, 35.5; 359/370, 577

[56] References Cited

U.S. PATENT DOCUMENTS

| | | | |
|---|---|---|---|
| 4,833,621 | 5/1989 | Umatate | 356/345 |
| 4,844,616 | 7/1989 | Kulkarni et al. | 356/359 |
| 4,953,188 | 8/1990 | Siegel et al. | 359/370 |

*Primary Examiner*—Samuel A. Turner
*Attorney, Agent, or Firm*—Kenneth M. Massaroni

[57] ABSTRACT

A high speed, high sensitivity inspection system (10) is provided, which is substantially impervious to external factors such as vibration. The inspection system is an optical system which employs phase contrast interferometry to achieve the desired results.

17 Claims, 6 Drawing Sheets

Particle Detect. 0.5x0.5 micr x 0.5 micr

FIG.5b

Pit Defect 1x1 micr x 75 nm

FIG.5c
Scratch Defect. 75x2 micr x 50 nm

FIG.5d
Coating Defect. 20x75 micr x 30 nm

DIFFERENTIAL PHASE CONTRAST INSPECTION SYSTEM

FIELD OF THE INVENTION

The invention relates generally to systems for optically inspecting high quality surfaces for sub-micron sized defects, and particularly to systems which use light beams to accomplish such inspection.

BACKGROUND OF THE INVENTION

Recently, manufacturers of virtually every type of electrical and electronic component have made significant strides in reducing component size. As sizes were reduced, it became increasingly important to assure that the fabrication of the components was free from defect. Defects on these increasingly small components could range down to a size of a few microns, or less. Cracks and scratches in glass substrates can have widths of less then 0.0003 mm, yet still propagate during the manufacturing process. Defects of even this size will therefore render many of today's electronic components inoperable.

Examples of electronic components requiring defect free surfaces include flat panel displays (FPD's) such as active matrix liquid crystal displays (AMLCD's), optical disks, optical flats, etalons and precision windows, prisms, and laser mirror substrates, to name but a few. Specific materials, such as transparent coated optics for use in LCD's and solar cells, also require surfaces that are free from defect. Added to the fact that defects in these materials can be as small as micron, is the fact that these devices or surfaces can have areas of one meter or more.

With respect to FPD's and particularly to AMLCD's, inspection is critical in that manufacturers report manufacturing yields of such devices at less then forty percent. One area which would provide substantial improvement to manufacturing yields would be to improve the quality of inspection of glass substrates prior to beginning the manufacturing process, after the deposition of preliminary layers of material, and during the overall process to screen for dust. Initial inspection of the substrates would screen for breaks, chips, cracks, warpage, and for veins and bubbles. Other key inspection criteria are for dust, scratches, and organic dirt.

It has long been known that the best way to inspect large area, high quality surfaces is to use light directed at the surface, and measure the amount of scattering, if any, caused by specific defects in the surface under investigation. A major problem has resulted from instances in which light beams reflected off of minute defects are scattered so slightly as to be indistinguishable from "noise" in the monitoring system. These types of situations typically arise when the defect is smaller than the diffraction limit of the light based system. Similarly, these problems will occur when the depth of the defect is less than the wavelength of the illuminating beam. These limitations in light scattering systems have rendered them unfit for inspecting extremely high resolution devices, since minute defects (although large enough to render the device inoperable) are undetectable by the system.

In an effort to overcome these shortcomings in light scattering systems, interferometric systems have been devised. Interferometry refers to measuring differences in the time or phase of two or more signals received by sensors spaced a known distance apart. These types of interferometric systems are widely known, and in laboratory usage today.

However, a major limitation of interferometric systems is that detection of the phase must be done in the specular direction since the wave fronts emerging from the source and the defect are overlapping in space (i.e., are propagating together). This results in a high DC level which must be overcome at the detection of the signal. Phase contrast interferometric methods overcome the problems associated with high DC level, but are extremely sensitive to adjustments, vibrations, mis-alignments, etc. Further, interferometric systems have fields with cyclical variations, and consequently a large oscillating phase term. Hence, the surface calculation becomes ambiguous since any point of the field can be interchanged with another, one wavelength distant. An additional limitation is the necessity for a reference beam, making the entire system sensitive to the reference adjustment within the space of a single wavelength.

These types of interferometric systems have proven successful, particularly in laboratory applications, since they possess heretofore acceptable sensitivity to defects, and are capable of discerning defects from background noise. Nonetheless, these types of systems have not proven useful in industrial settings. This is because their high sensitivity is easily effected by external influences, such as vibration and system adjustments.

Attempts have been made to eliminate these types of problems. The usual method of removing high DC levels present in interferometric systems is to apply phase contrast interferometry. This method provides adjustments to the two interfering beams of light so that the nominal optical path difference inside the system is one half of a wavelength. Consequently, after interference, the resulting amplitude is zero. Thus, a small change in one of the two interfering beams will result in a significant change in the resulting amplitude, and hence a significant measurement signal, free from a DC component.

The advantage of the phase interferometric system resides in the fact the phase contrast has a "zero" response to a "zero" signal, while a regular interferometric system has a "non-zero" reference level. The disadvantage of the phase contrast method is its extreme sensitivity and inflexibility to adjustments in the system. Any change in the nominal path length in the system will cause both a non-zero DC level, and a change in the signal contrast at the detector. This problem is exaggerated when high speed scanning is taking into account, as in industrial applications.

Further, and of major importance to manufacturers of FPD's and particularly to AMLCD manufacturers, is the fact that resolution levels for these type of systems remains below acceptable levels. For example, spatial resolution and depth resolution for conventional interferometers is approximately 2.0 µm and 0.01 µm respectively, while being extremely slow and unstable.

Accordingly, there exists a need for a light based inspection system with very high sensitivity to minute changes in the optical path (and hence the presence of defects on the investigated surface). The inspection system should be able to detect defects below the diffraction limit of the optical system, and be able to do so in a relatively fast manner. The inspection system should also have little or no influence from external factors.

OBJECTS OF THE INVENTION

It is therefore an object of the instant invention to provide a system capable of high accuracy inspection of high quality surfaces, having sub-micron size defects.

It is another object of the instant invention to provide an inspection system compatible with present day high surface quality production line techniques.

It is a further object of the instant invention to provide an inspection system capable of having high throughput.

It is yet another object of the instant invention to provide an inspection system capable of inspecting a variety of differently sized work pieces, without adjustment.

It is a yet further object of the instant invention to provide an inspection system that is impervious to vibration, misalignment, and other external factors.

These and other objects and advantages of the invention will become apparent from a perusal of the Detailed Description of the Invention, the Drawings, and the Claims which follow.

SUMMARY OF THE INVENTION

The instant invention overcomes the limitations of the prior art by providing a system wherein phase contrast is derived from a single beam of light, rather than by using two separate beams inside an interferometer. The inventive system, which the inventors have identified as a differential phase contrast, black beam interferometer, relies on the fact that the interference occurs entirely within a single beam of light.

This system employs a single beam of laser light which is modified across the wave front so as to produce a "black beam" in the surface plane. A "black beam" is a beam which has an intensity of zero in the vicinity of the optical axis.

The result is that when the undisturbed beam is detected (by a detector) close to the optical axis, the detector output is zero. However, if the beam encounters a defect, the balance will be upset, and the detector will register an output. If the beam scans over a defect, the varying detector output is a quantitative description of the defect. Defects can be represented by changes in any of the optical characteristics of the beam: amplitude, phase, or polarization.

This system provides several advantages over the prior art. For example, the system has high sensitivity in that both amplitude and phase of the defects are detected. As a result, even very shallow defects, i.e., with a height difference of a fraction of a wavelength, will be detected through phase changes. The system also offers high resolution, since a defect will affect the interferometric signal even if the size of the defect is far smaller than the size or wavelength of the illuminating beam. Consequently, the resolution of the system will not be limited by the beam size, but rather by the signal-to-noise ration in the system.

The system also provides high stability since it is a differential (i.e., common path) interferometric system. Thus, all aberrations, misalignments, movements, and external factors affect both beams, causing no path differences. Finally, the inventive system allows for high speed inspection of even large area substrates.

The inspection system of the instant invention includes a spatially coherent light source to illuminate the surface to be inspected. A phase plate is provided to impart a preselected pattern in the coherent beam of light. The object of the pattern is to modulate in a predetermined manner the phase of the wave front of the beam emitted by the source. A focusing system is also provided for focusing the illuminating beam onto the surface to be tested. The inspection system will also include a detector positioned to receive light reflected off of or transmitted by the surface to be inspected. The detector is capable of detecting changes in the interference structure of the received beam.

The inspection system may further include a scanning system, in either one or two coordinates, for allowing the inspection system to inspect the entire surface of a work piece.

DESCRIPTION OF THE PREFERRED EMBODIMENTS

The invention can be understood with reference to the following description, and drawings, in which reference numerals of the various drawings carry forward.

Figure 1:
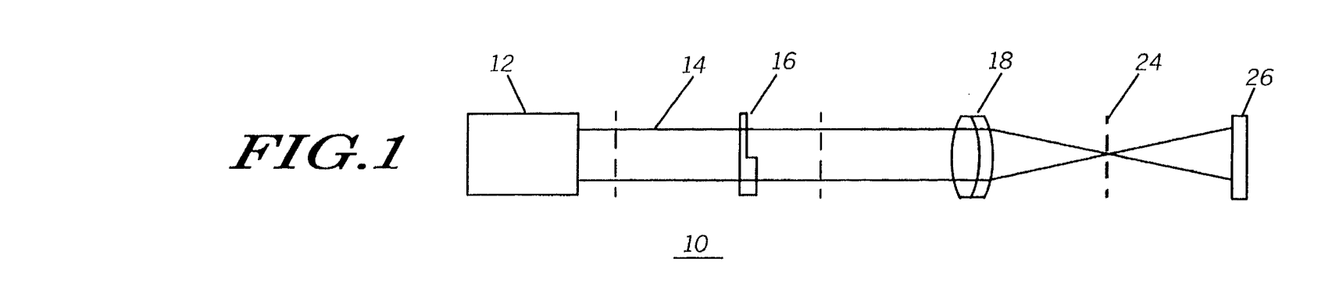
FIG. 1 is a simple block diagram of an inspection system in accordance with the invention.
Figure 2A:
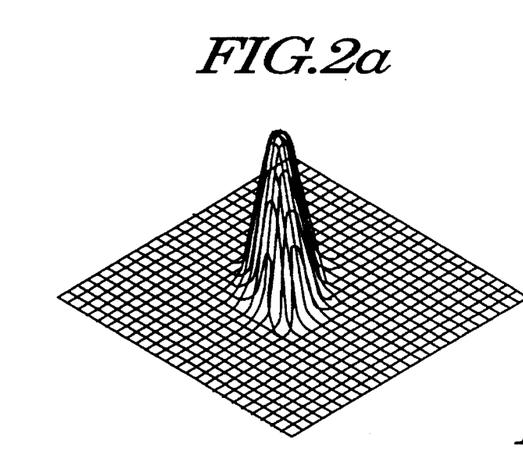
FIGS. 2A–2E illustrate light intensity and patterns as light passes through the elements of the inspection system of FIG. 1.
Figure 2B:
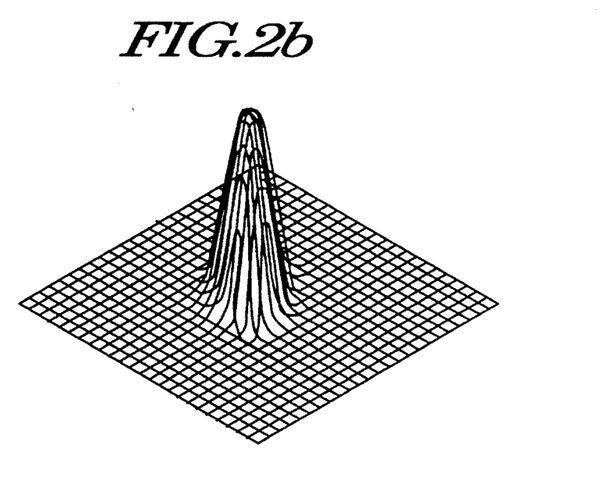

Referring now to FIG. 1, there is illustrated therein a simple block diagram of an inspection system 10 in accordance with the instant invention. The inspection system 10 includes a light source 12, which is preferably a coherent light source such as a laser. Light emitted from the coherent light source 12 is single phase light with a given intensity, as is illustrated in FIG. 2A. The light beam 14 is emitted from said coherent light source 12 and is directed towards an optical element 16. The optical element 16 is adapted to impart a phase retardation in given areas of the beam 14. In this regard, the optical element may be a phase plate, or other optical element adapted to introduce retardation into at least a part of the light beam 14. The phase retardation introduced into the light beam 14 can be, for example, a shift in the phase of the right side of the beam by one half of a wavelength relative to the left side of the beam. The phase and intensity of light emerging from phase plate 16 is illustrated in FIG. 2B.

The modified beam continues its propagation, and is passed through an optical lens 18. The lens 18 is adapted to generate a scan line in the focal plane on the surface of the item to be inspected. By using lens 18 to focus, the phase structure of the modified beam 14 interferes in the heal plane, and generates a focal plane pattern. The focused pattern will, in one preferred embodiment, have two lobes 20 and 22 of FIG. 2C. The two lobes are symmetrical, and the intensity at the origin is zero, hence providing the "black beam". The focal plane pattern is essentially the optical probe, and may be optimized to suit different inspection applications.

The focal pattern is then focused onto a work piece to be inspected 24. The work piece is in one embodiment a transparent work piece, such a glass substrate used in the manufacture of an FPD, or AMLCD. It is to be understood however, that the type of work piece upon which the inspection system is used does not limit in any way the instant invention. The optical black beam pattern propagates through the work piece 24, and reaches a detector 26. The detector 26 may have a linear sensitive area positioned at the zero intensity pattern of the focal plane pattern. The detector 26 may be, for example, a CCD, an amorphous silicon detection device, a PIN detector, or any other such optical detecting device as is known in the art.

Figure 2C:
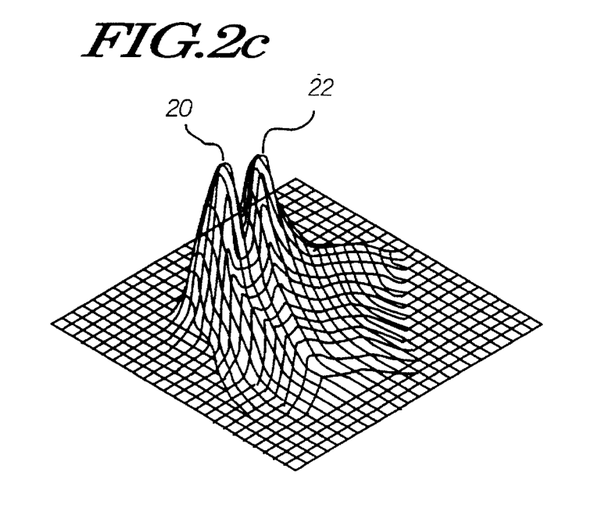
Figure 2D:
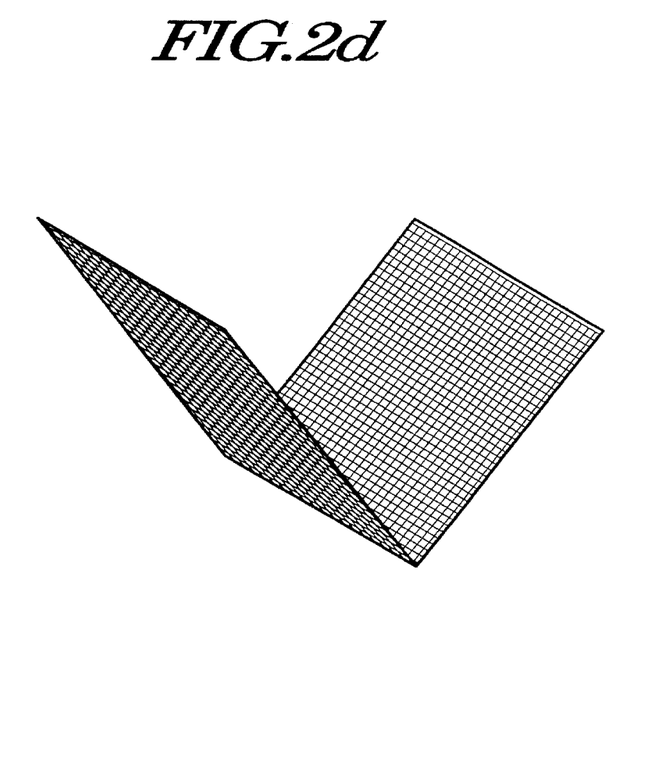
Figure 2E:
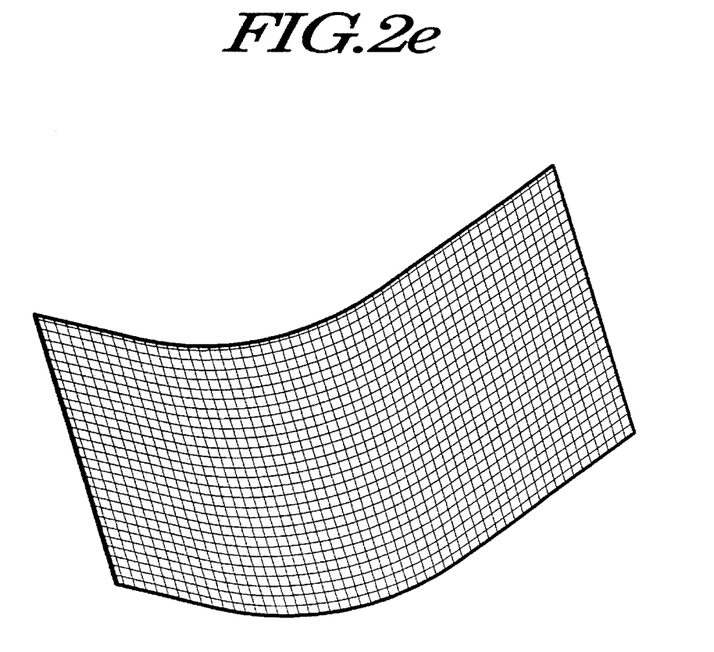

Assuming that the work piece 24 being inspected by the inspection system 10 is perfect, that is without defect, the modified, focused beam will reach the detector 26 without being disturbed or otherwise altered in terms of phase or amplitude. As a result, the beam detected at detector 26 will appear as illustrated in FIG. 2D. Conversely, if there is a defect in the work piece 24, the phase and/or amplitude of the light beam will be altered. That change in the beam will be detected at the detector 26, and may appear, for example, as is illustrated in FIG. 2E.

The principle behind the operation of the invention is that the electromagnetic field (optical beam) carries phase information about even the smallest structures in its path. Proper techniques can therefore resolve perturbations created by defects considered undetectable under normal conditions: defects of much smaller size (area) than the diffraction limit of the optics and much shallower (depth or height) than the wavelength of light. The technique used to resolve the minute perturbations mentioned above relies on a single coherent beam (rather than two or more beams) having a precise phase structure across the emitted wave front.

When focused, the phase structure of the beam cross-interferes due to beam propagation and diffraction. This produces intensity patterns across the beam. FIGS. 2A–2E illustrate the lobe (intensity) patterns resulting from a phase structure in which one half of the wave front has a phase shift of 180° relative to the other half. The effect of phase structuring can be seen in both amplitude and intensity of the structured beam. A phase-structured beam with the described phase pattern generates a specific intensity structure, the so called "black beam", since it has an intensity close to zero in the vicinity of the optical axis.

The "black beam" behaves like a differential interferometer working in a phase-contrast setup, with the important difference being that the two interfering beams are not and can not be separated through imaging means because they were generated by the diffraction of the same coherent beam. The inspection system therefore works as a single beam phase-contrast interferometer. The "black beam" can therefore be scanned, deviated, diffracted, focused or expanded, without losing the embedded phase information. A change affecting the entire structured beam will not change the structure, and will not affect the embedded information. The structured beam will also propagate without changing the embedded information over (practically) indefinite distances, as long as there are no changes within the wave front. It is this property that makes the inspection system substantially impervious to external factors such as vibration.

When the phase-structured "black beam" is made to pass through a work piece 24, such as a glass substrate, any defect generates a secondary wave which, when propagated further along the optical axis, interferes with the main black beam and upsets the delicate balance in the vicinity of the optical axis.

A non-zero reading by the detector 26 on the optical axis in a "black beam" will indicate the presence of a defect on the surface under inspection. The signature of the reading is an indication of the nature and size of the defect.

The phase structure in the beam of coherent light is produced by inserting a phase plate with a given pattern, into the path of the beam. As an example, the phase plate 16 may be which causes a phase change of lambda/2 between the two halves of the same diffraction limited beam.

The region being tested is illuminated by the focused "black beam" described above. After passing the test region, the structure of the beam is analyzed. A change in the wave front distribution as amplitude, phase, or polarization, will appear as a distinct alteration in the symmetry of the beam pattern. By evaluating the change in symmetry, one can record a defect as shown in the pattern observed in FIG. 2E.

Since any defect causes some change in the optical characteristics of the wave front, all defects are detectable limited only by the optical noise of the surface (generated by roughness) and the inspections system's own electrical noise.

The phase-structured laser light beam scans the entire surface being inspected, and a complete defect map of the surface is obtained. The map illustrates changes of the surface roughness and the position of defects as reflected in changes of the structure of the testing beam.

Figure 3:
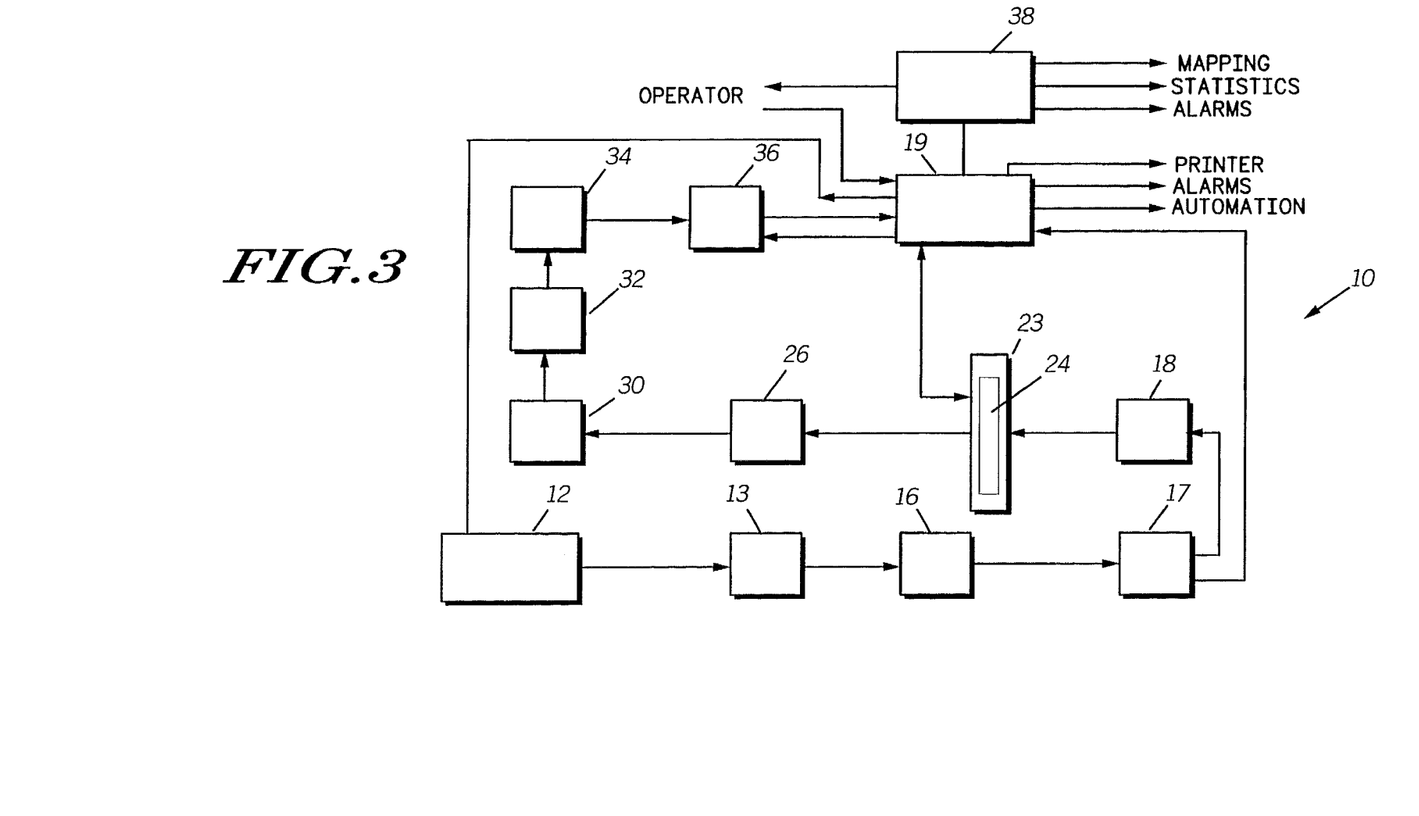
FIG. 3 is a functional block diagram of an inspection system in accordance with the invention.

Referring now to FIG. 3, there is illustrated therein a functional block diagram of an inspection system in accordance with the invention. From a coherent source 12 such as a laser an emitted beam 14 is filtered and collimated (expanded) by a spatial filter/beam expander 13, and passes through to the phase plate 16. The phase plate 16 introduces a phase retardation in given areas of the beam, specifically, the right side of the beam is phase shifted by half of a wave length relative to the left side.

The modified laser beam continues its propagation, having the phase information embedded in the beam structure. A servo mechanism 17 may be provided to control the beam position along the scan line. The scanning servo generates a signal which may go to a computer 19 so as to provide dimensional scanning. The servo, or alternatively a second servo provides movement of the work piece in the "y" coordinate. Specifically, scanning of the work piece is accomplished in both the "x" and "y" coordinate. The "y" coordinate is achieved by fast optical scanning as provided by the servo and computer. The "x" coordinate is accomplished by movement of the work piece relative to the inspection system. The "y" coordinate thus the position of the scanning spot along the scan line, while the "x" coordinate is the position of he scan line along the transport movement. The angular movement of the light beam over the lens 18 generates the scan line in the focal plane (the surface of the substrate being inspected). By focusing with the lens, the phase structure of the beam interferes in the focal plane.

The surface of the work piece 24 under inspection is positioned in the focal plane of scanning lens 18. The work piece 24 may be mounted in a frame/servo mechanism 23 which may move relative to the beam of light in response to signals generated by computer 19. As noted above, this movement provides the "x" coordinate of the two dimensional scan.

The laser beam having the "black beam" pattern imparted therein propagates through the work piece 24, and reaches the detector 26. If the tested surface is perfect, the phase pattern propagates in space without structural change, but with a scaling factor. Therefore the pattern on the detector will be similar to the one on the substrate at a larger scale. The detector 26 may have a linear sensitive area positioned along the "zero" intensity pattern in the scanned spot, and, for a "perfect" surface the signal is zero. The design of the detector may be optimized to be sensitive to the smallest change in the pattern. Therefore, any change affecting the symmetry of the lobe structure described in FIG. 2 creates a signal in the detector.

One of ordinary skill in the art can thus appreciate that, even if the system will not "see" the defect (or discriminate between two very close defects within the illuminating spot), an extremely small change in one of the lobes will affect the balance and generate a measurable signal.

One of the advantages of a system in accordance with the instant invention is that it will have a larger signal-to-noise ratio than a conventional interferometer (even when used in differential mode). The latter has a high DC bias, while the instant system inherently employs a "null reading" method, and is therefore limited only by electronic white noise (which is quite easy to filter).

The detector 26 is designed so that it may cover a large scanning field. The detection system has no collecting lens, and therefore, is not limited by the dimension of collecting optics. The scanning field is limited only by the detector's size. Therefore large inspection areas can be achieved in this configuration. The detector 26 will generate a signal in response to light incident thereon, which signal may be relayed to an amplifier 30. Electrical noise may be removed by a filter 32. The signal, which is essentially a measurement of the light incident on the detector, is digitized by an analog-to-digital converter board 34.

The thus digitized signal may be processed by, for example, a high speed Digital Signal Processing (DSP) board 36, which classifies the measurements, separates the amplifier noise, and reports the results (i.e., the presence or absence of defects) to the computer 19.

The computer 19 receives the signals, correlates them with the two signals received from the scanner 17 and related servo, and the frame/servo mechanism 23, and constructs a defect map for the work piece. The computer also serve as the man-machine interface, and the controls for system. The inspection system may also include input/ output devices, such as monitor 38, and printer outputs (not shown). Thus, the inspection results are displayed on the monitor, together with mapping, statistical information and other important operator information.

While the inspection system has heretofore been described for use with a transparent work piece, a non-transparent work piece could also be tested using a reflective methodology. The configuration of an inspection system to test reflective surfaces is similar to the configuration described for transparent surfaces. The main difference consists in the introduction of a beam splitter in the optical path of the illumination beam (from the laser). The surface of the work piece 24 would be illuminated through the beam splitter, with the signal being reflected back to the same beam splitter and then to a detector. In this configuration the detector is on the same side of the substrate as are the laser and the scanner.

Figure 4:
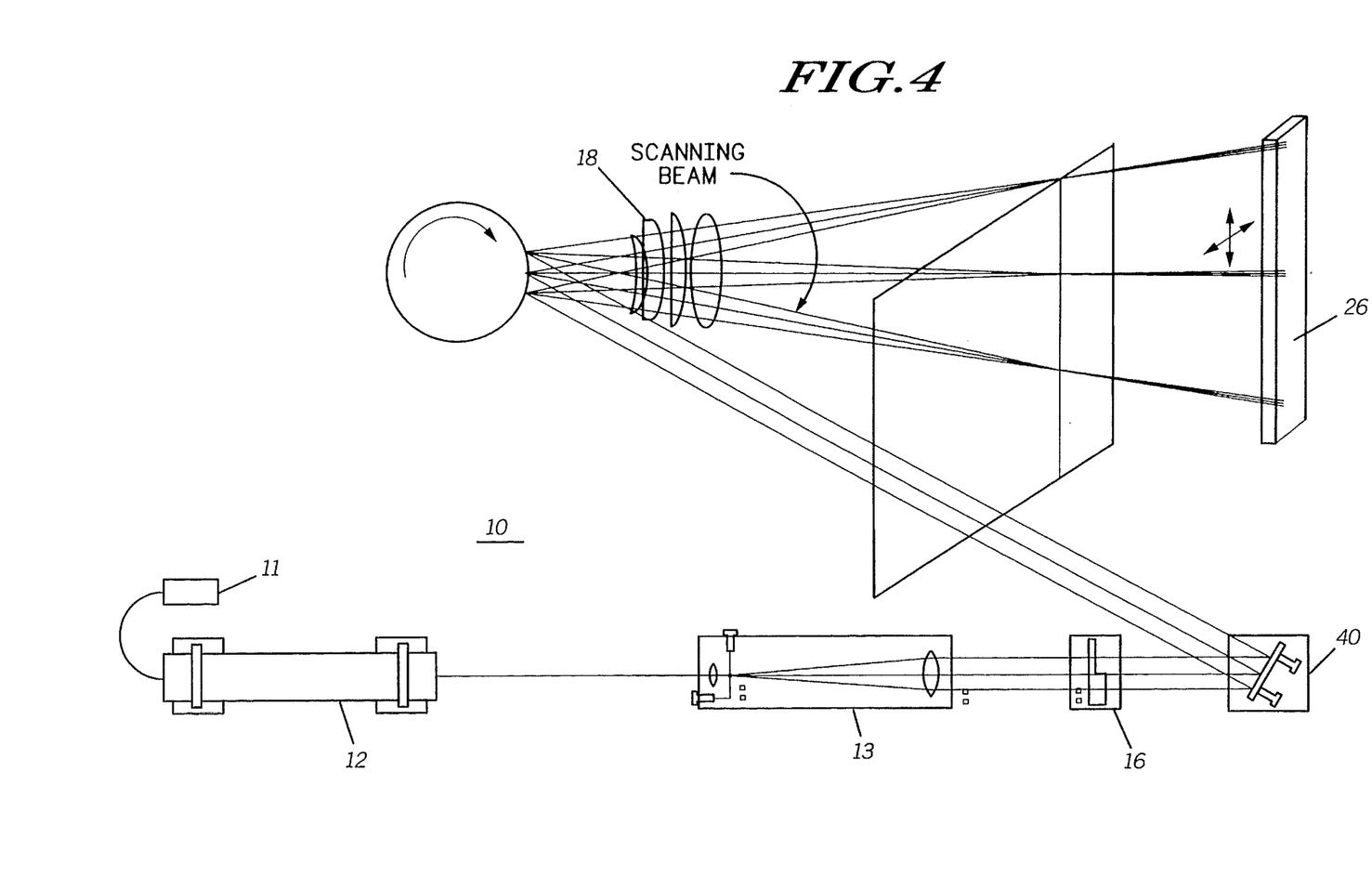
FIG. 4 is a schematic diagram illustrating the optical elements of an inspection system in accordance with the invention.

Referring now to FIG. 4, there is illustrated therein a schematic diagram illustrating the optical elements of an inspection system in accordance with the invention. The first element of the system is the laser 12, and as associated power supply 11. Mathematical modeling indicates that the light source should emit a high quality wave front ("perfect" Gaussian amplitude distribution and single phase), since any change in the wave front will be interpreted as a signal by the system. It can also be noted from modeling that small variations of the nominal wave length of the source are also relevant in the signal, due to the use of the phase plate in structuring the wave front. Therefore, the source should be a single point/single frequency diffraction limited emitter.

The light source 12 wave length is determined by the surface quality and detectability, and the inspection application itself. A smaller wave length increases the sensitivity of the system to both signal and noise. Mathematical simulations can optimize the wavelength according to the specific application.

General requirements for the light source 12 include: nominal wave length (based on mathematical simulations); wave length stability and noise (for optical noise considerations); nominal power output (from the standpoint of detection sensitivity); power noise; beam quality, i.e., spatial and temporal coherence; and pointing/scanning stability.

The next optical component illustrated in FIG. 4 is the spatial filter 13. The task of the spatial filter is to refine the laser beam wave front. Special attention must be given to the optimization of the filtering process: too little filtering is not efficient, too much will induce diffraction into the working beam.

The spatial filter can be tested and optimized by mathematical modeling. In general, the spatial filter should include characteristics of at least the following:

optical aberrations of the focusing objective pinhole quality beam-expanding ratio optical aberrations of the collimation objective collimation quality cosmetic quality of the collimation objective The next component of the inspection system 10, is the phase plate 16. The phase plate is designed to provide the optimum phase structure on the test surface. According to modeling, and depending on the type of detector selected, the phase plate can impart a number of phase patterns. In one preferred embodiment, a half wave optical path difference plate, configured in two halves and, as an alternative, four squares (quadrants). The beam pattern in the focal region is illustrated in FIG. 2C.

The phase plate(s) should be free from shape errors, and hence aberrations. The surface of the plate should be high quality to avoid noise. Care should be taken to avoid changes in the refractive index, thus distorting the light. Consideration must also be given to optical coating nominal thickness as optical path difference, optical coating thickness variations, and optical coating edge quality.

Though not discussed heretofore, the inspection system may include minors 40 to steer the light beam within the inspection mechanism. Such steering allows for economization in terms of overall design size. The requirements for the beam steering mirrors include: care in assuring the absence of shape errors, causing possible aberrations; overall high surface cosmetic quality for noise considerations; appropriate protective coating characteristics; and mechanical stability.

The scanning lens 18 has two main functions: to focus the beam to the required spot size and to provide the scan line. The size of the scanning spot is an important parameter in the system; it defines among other things: the testing sensitivity, the depth of focus (and, therefore, the mechanical tolerances), the testing speed and testing time, the frequency response of the electronics, the mapping accuracy, and the resolution of the servo systems.

The scan line defines the largest width possible to inspect in a single scan, and therefore, defines the throughput and the handling mechanism of the overall inspection system. Thus, aberration of the scanning lens must be kept to a minimum, since in operation (evaluating both amplitude and phase of the given wave front) a wave aberration is a major source of error. Due to the length of the scan line, the scanning lens 18 can be either telecentric or non-telecentric. In the latter case, the use of a field flattener in the vicinity of the focal plane may be necessary.

The last major optical component in the system is the detector 26. The detector translates the intensity of the field (optical signals) into electrical signals as described above. The maximum length of the detector relates to the maximum scan line, while the frequency response (together with the spot size) limits the scanning speed (and therefore, the testing time).

The detector 26 may have a high form factor (i.e., long and narrow) and may be designed for maximum frequency response. In order to increase the frequency response and to minimize the capacitance, the detector may be assembled from a number of smaller detection devices, butted in end-to-end fashion. The signal from each of the sub-detectors is independently evaluated.

The detector should be accurately positioned, with its dimensions determined by the actual lobe pattern which is a function of the spot size and the nominal position of the detection plane.

The detector 26 should be appropriately sized for a given application, and have a desirable frequency response. Moreover, given the size of the detector, appropriate mechanical rigidity should be built in. The detector should also possess high sensitivity, and be sensitive to small variations in intensity.

In one embodiment, the detector is a long, narrow photo diode, having dimensions of approximately 0.1 mm wide× 350 mm long. Silicon foundries are limited to wafers which are usually no more than 100 mm in diameter. Therefore, the detector may have to be fabricated from separate sections of silicon photo diode sensors. The sensitivity of the signal in the system is determined by the detector responsivity and the detector pre-amplifier noise level. One preferred pre-amplifier is a transimpedance amplifier, or current to voltage converter.

Simulation Results

Using a simulated inspection system in accordance with the invention described above with respect to FIGS. 1–4, favorable results have been obtained in the detection of minute errors in transparent substrates. Testing has been performed for the following working conditions:

| | |
|---|---|
| Laser wave length | 0.6328 µm |
| pattern size | approx. 10 µm |
| phase structure | lambda/2 step for half beam |
| substrate | transparent, clean |
| detector position | 10 mm behind substrate in axial direction |
| detector width | 100 µm sensitive area |

Figure 5A:
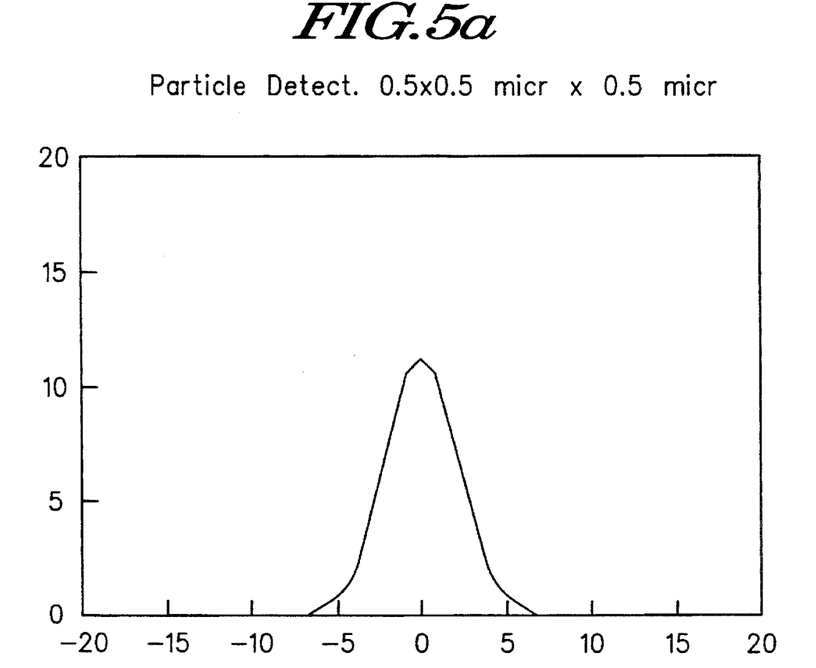
FIGS. 5A–5D illustrate the signature and intensity of the signal generated by various types of defect in a work piece.
Figure 5B:
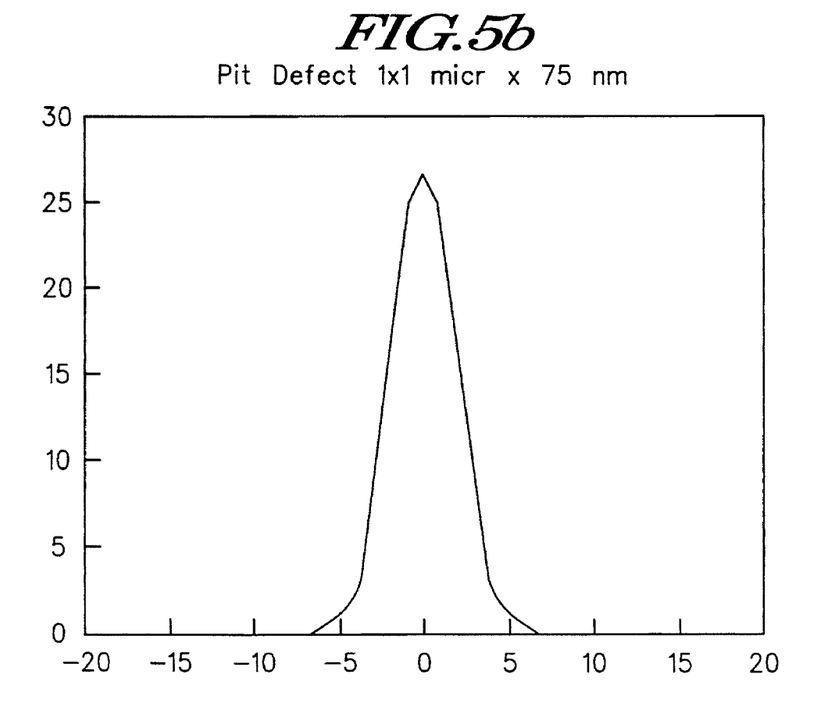

Using a device with the described features, a series of defects were scanned, with the results illustrated in FIGS. 5A–5D. FIG. 5A illustrates the signature and signal level generated by the inspection system in response to detecting a point defect, specifically a particle on the substrate surface, having dimensions of 0.5 µm width×0.5 µm length×0.5 µm height. Similarly, FIG. 5B illustrates the signature and signal level generated by the inspection system in response to detecting a point defect, specifically a pit in the substrate surface, having dimensions of 1.0 µm width×1.0 µm length× 0.075 µm depth.

Figure 5C:
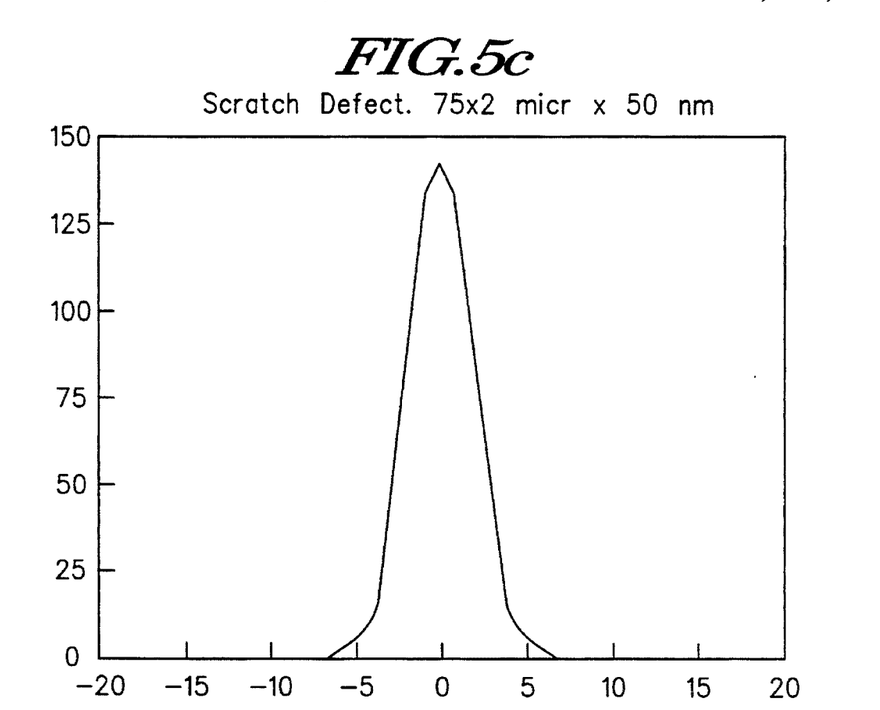
Figure 5D:
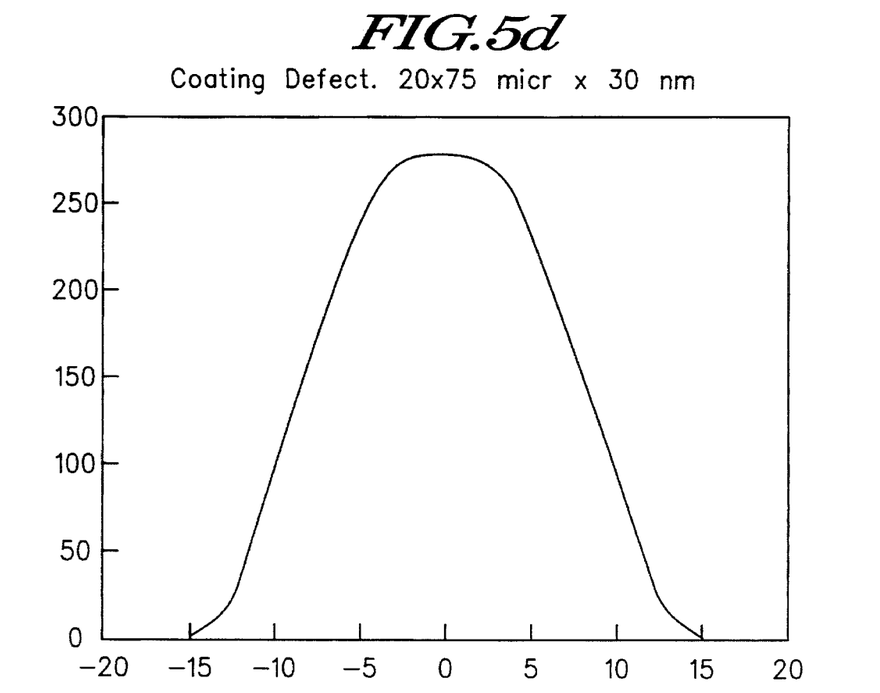

Defects in the nature of scratches are also easily detectable by the inspection system. For example, FIG. 5C illustrates the signature and signal level generated by the inspection system in response to detecting a scratch in the substrate surface. The scratch had dimensions of 2.0 µm width×75.0 µm length×0.050 µm depth. In this way, it is also possible for the inspection system to detect the absence of sections of coating on a coated substrate. FIG. 5D illustrates the signature and signal level generated by the inspection system in response to detecting a defect in a layer of coating applied to a substrate surface. The surface defect had dimensions of 20 µm width× 75 µm length×0.035 µm depth.

As may be readily appreciated by those skilled in the art, the present invention can be practiced other than as is specifically disclosed herein. Thus, while the instant invention has been described with respect to certain preferred embodiments, it is to be understood that the foregoing and other modifications and variations may be made without departing from the spirit or scope of the invention.

We claim:

1. An inspection system comprising:
   a laser light source for emitting a beam of laser light having an optical axis:
   a phase plate operatively disposed in the path of light emitted from said laser light source, said phase plate adapted to modulate the phase of the wave front of at least part of said beam, and impart a pattern on said beam so that the intensity of said beam in the vicinity of the optical axis of said beam is substantially zero;
   a spatial filter means operatively disposed between said light source and said phase plate, said spatial filter means adapted to refine the wave front of light emitted from said laser light source;
   a focusing system for focusing light modified by said spatial filter and said phase plate onto a predetermined area;
   an inspection stage upon which items to be inspected are mounted; and
   detector means operatively positioned relative to said stage so as to receive light after interaction with items inspected on said stage, said detector being adapted to generate an electrical signal in response to light incident thereon.

2. The inspection system of claim 1, further including means for directing said beam of light over at least one dimension of the surface of said work piece.

3. The inspection system of claim 2, wherein said directing means comprises an optical scanner.

4. The inspection system of claim 3, wherein said optical scanner is a polygon scanner, and said scanner is adapted to scan said work piece in a first dimension.

5. The inspection system of claim 1, further including means for moving said stage relative to said light source, said movement means controlled by a computer.

6. The inspection system of claim 1, wherein said phase plate modifies half of said beam of light by a factor of lambda/2 relative to the unmodified half of said beam.

7. The inspection system of claim 1, further including at least one mirror for redirecting the path of light emitted from said light source.

8. The inspection system of claim 1, wherein the item to be inspected is substantially transparent so that light from said light source passes therethrough, and said detector is operatively disposed on the side of said workpiece opposite said light source.

9. The inspection system of claim 1, wherein the item to be inspected is substantially opaque, so that light from said light source is reflected from it, and said detector is operatively disposed on the same side of said workpiece as said light source.

10. The inspection system of claim 1, wherein defects in said workpiece are detected when said defects alter the light beam so that the intensity of the light along the optical axis is greater than zero.

11. A method for determining the presence of defects in the surface of a work piece, said method comprising the steps of:

provising a source of coherent light having an optical axis;

modifying the phase of said coherent light so that the intensity of said light at the optical axis is substantially zero;

directing said light through a work piece; and measuring the intensity of said light beam at the optical axis after passing through said work piece.

12. The method of claim 11, wherein said coherent light source is a laser light source.

13. The method of claim 11, wherein the step of modifying said light source includes the further steps of first passing said light through a spatial filter, and then passing said light through a phase plate adapted to modify at least one side of said light beam by an amount equal to approximately lambda/2 relative to the unmodified side of said beam.

14. The method of claim 11, including the further step of focusing said light beam onto said work piece so as to define a area to be scanned, and to define a dimension along which to scan said work piece.

15. The method of claim 11, including the further step of providing means to effect relative movement between said light source and said work piece.

16. The method of claim 11, including the further step of providing minors for redirecting light.

17. The method of claim 11, wherein the intensity of said light after passing through said work piece is measured by a detector capable of generating electrical impulses in response to light incident thereon.

* * * * *